United States Patent [19]

Siegel

[11] Patent Number: 4,887,594
[45] Date of Patent: Dec. 19, 1989

[54] VIBRATORY MEDICATOR

[76] Inventor: Louis Siegel, 500 Grosvenor Rd., Rochester, N.Y. 14610

[21] Appl. No.: 204,398

[22] Filed: Jun. 9, 1988

[51] Int. Cl.[4] .............................................. A61H 1/00
[52] U.S. Cl. ......................................... 128/36; 128/65
[58] Field of Search ................................. 128/34–36, 128/32, 56, 57, 62 R, 65

[56] References Cited

U.S. PATENT DOCUMENTS

| | | | |
|---|---|---|---|
| 1,573,639 | 2/1926 | Fischer | 128/35 |
| 1,594,636 | 8/1926 | Smith | 128/32 |
| 1,630,115 | 5/1927 | Duprey | 128/36 |
| 1,772,501 | 8/1930 | Shelton | 128/32 |
| 1,896,351 | 2/1933 | Doran | 128/36 |
| 1,947,042 | 2/1934 | Glennan | 128/57 |
| 2,324,337 | 7/1943 | Jomsland | 128/36 |
| 2,703,571 | 3/1955 | Thomas | 128/36 |
| 2,709,432 | 5/1955 | Ackerman | 128/57 |
| 3,557,781 | 1/1971 | Kaye, Sr. | |
| 3,636,946 | 1/1972 | Hardy | 128/57 |
| 3,789,842 | 2/1974 | Froimson | |
| 3,967,617 | 7/1976 | Krolik | 128/36 |
| 3,970,081 | 7/1976 | Applegate, Jr. | |
| 4,098,266 | 7/1978 | Muchisky et al. | |
| 4,343,303 | 8/1982 | Williams | |
| 4,427,001 | 1/1984 | Kiefer et al. | 128/57 |

Primary Examiner—Edgar S. Burr
Assistant Examiner—Huong Q. Pham
Attorney, Agent, or Firm—Stonebraker, Shepard & Stephens

[57] ABSTRACT

A vibratory medicator combines a medication dispenser (35, 40, 45) with a vibrator (10) containing a motor-driven eccentric mass (13). The vibrator body (15) can be either hand held or strapped in place against a skin region to be treated; and when body (15) is vibrated, it vibrates the medication dispenser, which is pressed against the skin to apply the medication to the skin and to transmit vibrational energy to the skin. This provides the known benefits of vibration and also enhances the penetration of the medication into the skin region being treated.

11 Claims, 3 Drawing Sheets

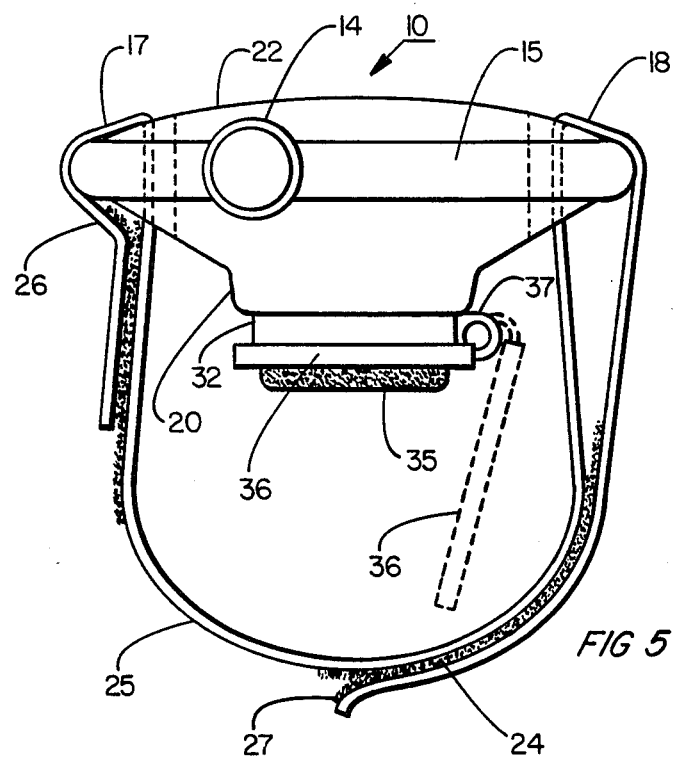
FIG 5
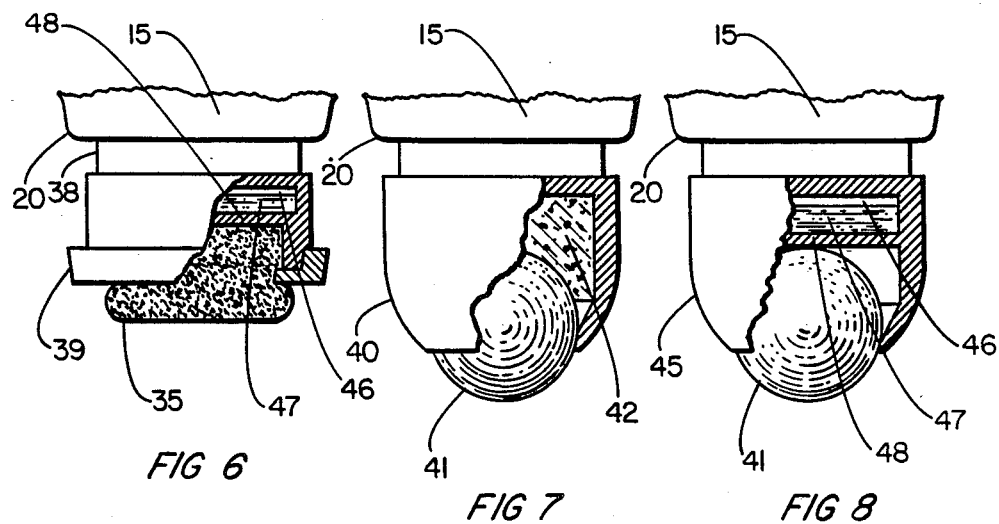
FIG 6
FIG 7
FIG 8

VIBRATORY MEDICATOR

BACKGROUND

Vibrators applying a vibrational motion to the skin are known to soothe the treated region and to stimulate blood circulation, which facilitates removal of edema and products of inflammation to alleviate pain and promote healing. A variety of medications have also been applied to the skin over pained or injured regions to proomote healing. Medicated regions of the skin have also been mechanically vibrated, to combine the beneficial effects of the medication and the vibration.

To simplify and improve the delivery of both medication and vibration, I have devised a way that a medication dispenser can be combined with a vibrator so as to deliver a medication to a skin region that is being vibrated. My way of doing this conveniently and effectively mounts a medication-containing dispenser on a vibrator so that the medication dispenser itself vibrates against the skin to both dispense the medication and also enhances its penetration into the skin. My vibrator can be hand held or strapped onto the user's body to apply medication and vibration to a skin region, and my system combines several features making vibrational medication delivery convenient, quick, and comfortable. Because of its simplicity and ease of use, my system can be used at home for daily treatments of ailments such as tennis elbow or muscle pains and spasms, for example.

SUMMARY OF THE INVENTION

My vibratory medicator includes a hand-holdable body containing a motor-driven eccentric mass arranged for vibrating the body. A strap threaded through a strap loop on the body is arranged for strapping the body against a skin region to be treated and medicated, so that the body can be either hand held or strapped in place. A medication-containing dispenser is mounted on a working surface of the body and vibrates with the body. The dispenser is disposed so that a hand holding the body can press the dispenser against the skin region and so that a strap holding the body also presses the dispenser against the skin region. The medication is loaded into the dispenser on the vibrator body, and the body is vibrated while pressing the dispenser against the skin. The vibration not only facilitates dispensing medication from the dispenser into contact with the skin, but also enhances the penetration of the medication into the skin to help the medication work.

DRAWINGS

FIG. 5 is a side elevational view, similar to the view of FIG. 4, and schematically showing an alternative retainer for a dispenser using a medication-soaked pad.

FIG. 6 is a fragmentary side view, similar to the views of FIGS. 4 and 5, and showing an alternative retainer for holding a medication-soaked pad as a dispenser.

FIG. 7 is a fragmentary and partially schematic side view of a roller ball for dispensing medication from my vibrator.

FIG. 8 is a fragmentary and partially schematic side view of an alternative form of roller ball for dispensing medication from my vibrator.

DETAILED DESCRIPTION

Figure 3:
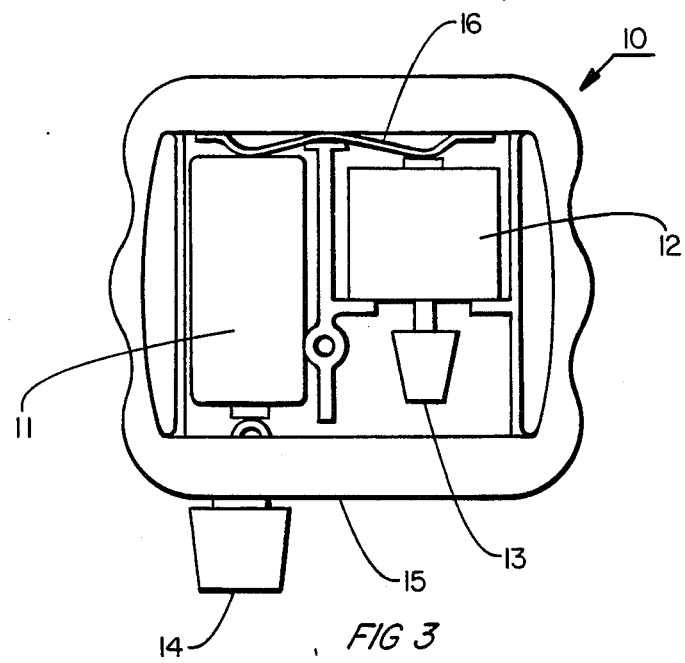
FIG. 3 is a partially schematic plan view of the vibrator of FIG. 2, with the cover removed from the vibrator.

My vibrator 10 for medicating a region of the skin is small, portable, and capable of being held in a hand and manually pressed against the skin. It uses a motor 12 for rotating an eccentric mass 13 that causes the body 15 of vibrator 10 to vibrate. Motor 12 can be powered by AC, via a cord, but for easy portability, I prefer a battery 11, as shown in FIG. 3. A switch (not shown) within a knob 14 turns vibrator 10 on and off. A timer can be included for operating the switch or an indicator to ensure that the vibration is turned off after a predetermined interval, or that the vibration is turned both on and off at set intervals.

Battery 11 and motor 12 are pressed into their operating positions, as shown in FIG. 3, by an electrically conductive spring 16 that engages both battery 11 and motor 12. Spring 16 serves the dual purposes of conducting electricity from battery 11 to motor 12 and also spring biasing both of these components into their illustrated operating positions. The complete circuit back to the switch is not shown.

Body 15 has at least one strap loop 17 to accommodate a strap that can hold body 15 against the skin, and I prefer a pair of strap loops 17 and 18 arranged along opposite edges of body 15. I also prefer that finger-gripping recesses 19 be formed along the outer edges of strap loops 17 and 18 to afford a comfortable finger hold along the edges of body 15.

Figure 4:
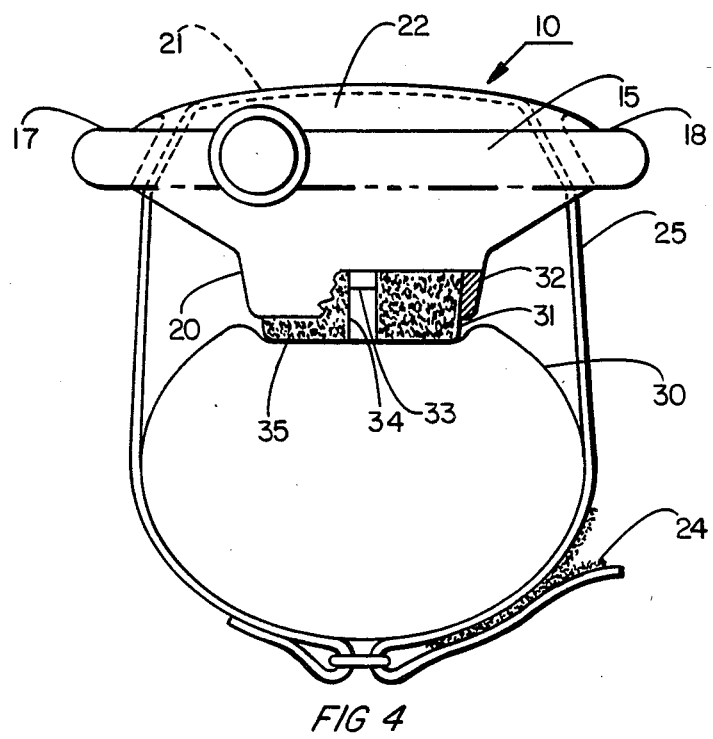
FIG. 4 is a partially cutaway, side elevational view of the vibrator of FIGS. 1-3 strapped around a schematically illustrated arm to show vibratory medication delivery via a dispenser using a medication-soaked pad.

The pair of strap loops 17 and 18 cooperate with a strap groove 21 on the top or non-working face 22 of body 15, opposite working side 20. Strap groove 21 and the two strap loops 17 and 18 allow two different ways of strapping body 15 in place. One of these, as shown in FIG. 4, uses a strap 25 that passes through loop 17, over the top 22 of body 15 in strap groove 21, and down through strap loop 18 so that strap 25 can wrap around a schematically illustrated arm 30. I prefer a hook and loop pile fastener 24 for fastening an end region of strap 25 to hold body 15 against arm 30. Straps of different lengths can be arranged for holding vibrator 10 against the skin in different regions of the human body for vibratorily medicating those regions; and if strapping body 10 in place is not practical or convenient, it can be hand held during treatment.

An alternative and preferred strapping arrangement is shown in FIG. 5, where strap 25 has an end loop 26 passing through strap loop 17 and fastened to itself to secure strap end 26 in strap loop 17. From there, strap 25 wraps around an arm or other body part, passes through strap loop 18, and folds back on itself to be fastened with a hook and loop pile fastener 24. I prefer the strapping arrangement of FIG. 5, because it can pull body 15 snugly against the skin, without tending to twist or roll body 15 out of position. One hand can pull on the free end 27 of strap 25 to snug vibrator body 15 against the skin, and then fastener 24 can hold strap 25 and body 15 in this position.

Figure 1:
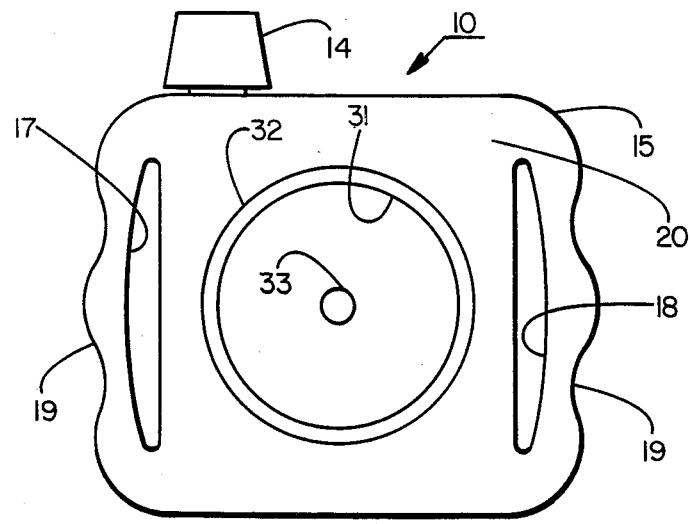
FIG. 1 is a plan view of a working side of a preferred embodiment of my vibratory medicator.
Figure 2:
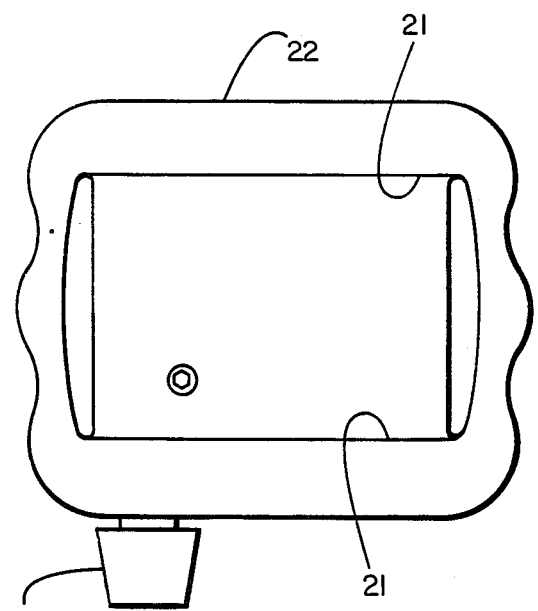
FIG. 2 is a plan view of the top or hand-holdable side of the vibrator of FIG. 1.

An important component of vibrator 10 is a medication-containing dispenser mounted on bottom or working surface 20. One simple form of medication dispenser is a medication-soaked pad 35 held in a retainer 31 on the working face 20 of body 15 where pad 35 both contains and dispenses medication. As shown in FIGS. 1 and 4, retainer 31 can be a shallow socket having a rim 32 that holds a disk-shaped medicator pad 35. A central pin 33, shorter than the height of rim 32 extends into a central hole 34 and helps retain pad 35 in place in retainer socket 31.

Pad 35 is presoaked with a medication to be applied to the skin and is preferably sold in a container holding several soaked pads delivered one at a time, to be used and discarded. A soaked pad 35 can then be removed from the container and placed in retainer socket 31 for use. When loaded with pad 35, vibrator 10 is pressed against the skin region to be treated, as shown in FIG. 4, either by hand or strap pressure; and vibrator 10 is vibrated so that medicated pad 35 vibrates against the skin. The vibrational energy from vibratory body 15 is transmitted to the skin via medicated pad 35, which also dispenses the medication onto the outer surface of the skin. The vibrational energy stimulates blood circulation and also facilitates the penetration of the medication into the skin. The simple pressing and vibrating of the medicated pad 35 against the skin accomplishes both the beneficial effects of vibrating the region to be treated and the healing enhancement derived from the medication and its penetration into the region being treated.

Many different medications can be used with vibrator 10 for many different purposes, and my system is not limited to any particular medication. Suitable medications can include lotions, creams, ointments, liniments, balms, oils, and pain relievers, as well as chilling or heating materials. The medical effects of all of these are well-understood, and there is evidence from trials of my system that the beneficial effects of medications are enhanced by vibrationally delivering them to the region being treated. This may be partly because vibration enhances the medication delivery, and partly because vibration enhances the penetration of the medication into the skin.

There are other ways of retaining medicated pad 35 in place on working surface 20 of vibrator body 15. In FIG. 5, for example, a bezel or retainer ring 36, having a hinge 37, can be snapped down over retainer rim 32 to hold medicated pad 35 in place. The periphery of pad 35 is compressed by ring 36 so that it bulges outward in the center of ring 36, as illustrated, and contacts the skin within the open area of ring 36.

Medication dispensers can also be interchangeable, as shown in FIGS. 6–8. A dispenser 38, using a medicated pad 35, as shown in FIG. 6, can be interchanged with roller ball dispensers 40 and 45, using a roller ball 41, as shown respectively in FIGS. 7 and 8, by intercoupling means such as a bayonet joint (not shown). The user can then select the medication dispenser most suitable for a particular treatment and can fasten the dispenser onto the working face 20 of vibrator body 15.

Dispenser 38, using medicated pad 35, has a bezel or ring 39 that threads onto dispenser 38 to compress and retain pad 35. This is an alternative to hinged retainer ring 36 of FIG. 5, which is preferred for ensuring that the retainer ring does not become separated and lost.

Dispenser 40, as shown in FIG. 7, includes a roller ball 41 wetted by a medication-soaked dispenser pad 42 that provides a reservoir of medication. The user removes roller ball dispenser 40 from body 15, inserts a medication-soaked pad 42 behind ball 41, attaches dispenser 40 to working face 20, and then operates the vibrator to vibrate ball 41 against the skin. The vibrator is preferably hand held while doing this, so that ball 41 can be rolled around the skin region to be treated. Medication in pad 42 wets the surface of ball 41 as it rolls. This applies medication to the skin while transmitting vibration through ball 41 so that both the medication dispersement and its penetration into the skin are enhanced by the accompanying vibration.

Dispenser 45 of FIG. 8, also using a roller ball 41, is similar to dispenser 40 except for using a reservoir 46 of a medication 47 applied to roller ball 41 via a valve or metering aperture 48. This wets the surface of ball 41 as it rolls about the skin to achieve the same effect described relative to dispenser 40 of FIG. 7. A reservoir 46, containing a medication 47, can also be arranged for wetting dispenser pad 35 pressed against the skin, as shown in FIG. 6, or for wetting pads such as pad 42 of FIG. 7, used to wet a roller ball. There are many other variations on ways that a roller ball can be wetted with medication, while being vibrated against a skin treatment region to accomplish the vibratory medication delivery of my system.

I claim:

1. A vibratory medicator comprising:
   a. a body shaped and sized to be held within a hand so that a palm of said hand can press a working surface of said body against a skin region to be medicated, said body containing a motor-driven eccentric mass arranged for vibrating said body against said skin region;
   b. each opposite side of said body having a strap loop grippable by a hand and arranged so that both loops span a strap line and allow a strap extending along said strap line to be threaded through said strap loops for strapping said body against said skin region to be medicated;
   c. a vibratory medication dispenser mounted on said working surface of said body in between said strap loops and opposite a surface of said body engaged by a hand holding said body so that said medication dispenser vibrates with said body against said skin region;
   d. said working surface being disposed on said body so that a hand holding said body can press said medication dispenser vibrationally against said skin region, and so that said strap threaded through said strap loops can hold said body against said skin region to press said medication dispenser vibrationally against said skin region;
   e. vibration of said body with said medication dispenser pressed against said skin region being arranged for delivering said medication from said dispenser to said skin region and enhancing the penetration of said medication into said skin region; and
   f. a battery and a motor for driving said eccentric mass are each pressed into position in said body by a single, electrically conductive spring that presses said battery against an electric terminal, and presses said motor against an abutment, while conducting electricity from said battery to said motor.

2. The vibratory medicator of claim 1 wherein said medication dispenser is a medication-soaked pad held within a pad retainer on said working surface of said body.

3. The vibratory medicator of claim 2 including a hole in said medicated pad and a pin in a central region of said retainer for fitting in said hole in said pad without extending all the way through said pad.

4. The vibratory medicator of claim 2 including a ring extending around and separably attached to said retainer for securing said medicated pad within said retainer.

5. The vibratory medicator of claim 4 wherein said retainer ring is hinged on said body adjacent said retainer.

6. The vibratory medicator of claim 2 wherein said medication dispenser includes a reservoir and a passageway for admitting medication from said reservoir to said medication-soaked pad.

7. The vibratory medicator of claim 1 wherein said medication dispenser includes a socketed spherical roller ball that can be moved over said skin region to be medicated.

8. The vibratory medicator of claim 7 including a medicated pad arranged within a socket for said roller ball for applying medication to said roller ball as said roller ball turns in said socket.

9. The vibratory medicator of claim 7 wherein said medication dispenser includes a reservoir and a passageway for admitting medication from said reservoir to a socket for said roller ball.

10. The vibratory medicator of claim 1 including finger grip recesses arranged on a periphery of said body in the region of said strap loops.

11. The vibratory medicator of claim 1 including a strap groove extending between said strap loops over said body opposite said working surface.

* * * * *